(12) United States Patent
Silber et al.

(10) Patent No.: US 7,332,150 B2
(45) Date of Patent: Feb. 19, 2008

(54) ABRASIVE COMPONENT FOR A CLEANING AGENT IN A CLEANING PRODUCT INTENDED FOR USE ON DELICATE SURFACES, ESPECIALLY ON TEETH

(75) Inventors: Gert Ulrich Silber, Ponte Capriasca (CH); Beat Kilcher, Bosco Luganese (CH); Beat A. Von Weissenfluh, Gentilino (CH)

(73) Assignee: KerrHawe S.A., Bioggio (CH)

( * ) Notice: Subject to any disclaimer, the term of this patent is extended or adjusted under 35 U.S.C. 154(b) by 493 days.

(21) Appl. No.: 10/433,922

(22) PCT Filed: Dec. 8, 2000

(86) PCT No.: PCT/CH00/00655

§ 371 (c)(1),
(2), (4) Date: Jun. 6, 2003

(87) PCT Pub. No.: WO02/45676

PCT Pub. Date: Jun. 13, 2002

(65) Prior Publication Data

US 2004/0042976 A1    Mar. 4, 2004

(51) Int. Cl.
*A61K 8/00* (2006.01)
*A61K 8/18* (2006.01)
*A61Q 11/00* (2006.01)

(52) U.S. Cl. .............. 424/48; 424/49; 433/216

(58) Field of Classification Search ............. None
See application file for complete search history.

(56) References Cited

U.S. PATENT DOCUMENTS 2,059,396 A * 11/1936 Ripert ..................... 424/49
4,692,480 A * 9/1987 Takahashi et al. ........ 523/218
6,248,806 B1 * 6/2001 Codolar et al. .......... 523/177

FOREIGN PATENT DOCUMENTS

| BE | 406912 | 12/1934 |
|----|--------|---------|
| EP | 0 318 168 A2 | 5/1989 |
| EP | 1 050 293 A1 | 11/2000 |
| EP | 1 051 962 A1 | 11/2000 |
| RU | 2 098 466 C1 | 12/1997 |

OTHER PUBLICATIONS

Chemical Abstract 1981:66934, "Lamellar organic glass", abstract of Russian patent SU 765333 (1980).*
Chemical Abstract 1969:51550, "Lamellar glass-crystal structures in the system ZnO-B2O3", abstract of Journal of Crystal Growth 3-4, 674-8 (1968).*

* cited by examiner

*Primary Examiner*—Frederick Krass
(74) *Attorney, Agent, or Firm*—Wood, Herron & Evans, LLP

(57) ABSTRACT

A material is proposed as an essential abrasive component for cleaning agents in cleaning products for delicate surfaces which is essentially composed of platelets. These platelets are preferably shaped without sharp points, i.e. their circumference is similar to a polygon whose corners do not show angles that are in the majority smaller than 30° and greater than 330°. Glass flakes are for example such a material. The abrasive component of the invention may for example be used for the manufacture of toothpastes and prophylaxis pastes that are efficient but nevertheless not harmful to teeth.

7 Claims, 1 Drawing Sheet

ABRASIVE COMPONENT FOR A CLEANING AGENT IN A CLEANING PRODUCT INTENDED FOR USE ON DELICATE SURFACES, ESPECIALLY ON TEETH

This application claims priority to International Application No. PCT/CH00/00655, filed Dec. 8, 2000, the disclosure of which is hereby incorporated herein by reference in its entirety.

The present invention relates to an abrasive component for cleaning agents according to the preamble of claim 1. The invention is especially related to abrasive components in dental care products.

The following description refers in particular to tooth cleaning products. It applies, however, by analogy to care products for delicate surfaces in general.

Toothpastes (dentifrices) are cleaning agents for the daily individual dental care as a prophylactic measure against, inter alia, caries, gingivitis and periodontitis. Prophylaxis pastes, on the other hand, are products that are professionally used by the dentist and/or the dental hygienist in order to remove adherent deposits, such as stain, plaque and tartar that are solidly sticking to the surface of the tooth crowns or the dental roots. Prophylaxis pastes are therefore generally used on slowly rotating paste carriers and exhibit in any case a substantially stronger cleaning power as well as a different consistency than toothpastes.

In order to classify toothpastes and prophylaxis pastes, REA and RDA values are used among other parameters. REA values refer to the relative abrasion of enamel, while RDA values relate to the relative abrasion of dentine. The respective measuring method is described in the *Journal of Dental Research* 55/4 (1978), 563. It should, however, be noticed that REA/RDA values of toothpastes cannot be directly compared to those of prophylaxis pastes. REA/RDA values are only useful for the comparison of toothpastes among each other or of prophylaxis pastes among themselves, respectively.

Another important feature of quality of dental care products is the extent of induced surface roughness (average roughness depth) and of scratch-formation (maximum roughness depth) during their use. Surface roughness is measured by means of-surface scanning devices, scratches can also be determined qualitatively using a microscope.

One of the most important components of cleaning products having an abrasive effect, such as dental care products, is the abrasive agent. If the cleaning product is to be used on delicate surfaces, such as, in particular, dental hard tissues such as dentine, cementum and enamel, or restoration surfaces of composite or ceramic materials, but also lacquer surfaces or high gloss polished metallic surfaces, the abrasive must meet the following requirements: It must have the best possible cleaning effect, while at the same time abrading the cleaned surface as little as possible. It must further smoothen the surface and preferably also polish it while simultaneously best possibly avoiding to produce scratches. Up to now one has tried to solve this problem in dental care products by incorporating hard materials into the formulations preferably in the form of finely dispersed particles in order to avoid the formation of scratches in dental hard tissues and restoration surfaces while maintaining the polishing effect.

The following materials have been proposed in the literature for use as abrasives in dental care products. The listing is not exhaustive, it is rather meant to show that the problem of the correct selection of abrasives for dental care products can by no means be considered as resolved: calcium carbonate, barium carbonate, precipitated lime, chalk, whiting, flour of pumice, calcium and magnesium phosphate, magnesium carbonate, zeolites, reef limestone, talcum, kaolin, bone substances, kieselguhr, aluminum oxide, silicon dioxide and silicates, powdery synthetic substances, etc., and all possible variants thereof. A review is given in the document BE-A-406 912 where it is further suggested to use only such substances as abrasives in tool cleaning products that have a hardness not exceeding that of dental enamel, namely a Mohs hardness between 2 and 3. Mica is mentioned among others as an example.

The document EP-A-268 763 discloses the use of precipitated silicic acid together with expanded Perlite as a second abrasive component in prophylaxis pastes. A prophylaxis paste containing Perlite as an abrasive is described in EP-A-528 756, and a Perlite containing toothpaste is the subject of WO-A-94/1557. The last two patent applications have been filed by the applicant of the present document.

Expanded Perlite, when ground, consists of sharp-edged, eggshell-shaped fragments that are broken down during their use into smaller fragments. This results in a transition from a high to a low abrasive effect which may be compared to a transition from grinding to polishing. In order to master such cleaning agents, it is essential to control both particle size as well as particle structure. During the grinding process of the Perlite raw material, transition zones (spandrels) between single fused Perlite bubbles form particles which will not break down into smaller fragments during use to the same extent as the above mentioned eggshell-shaped fragments. Such spandrel particles are honeycomb-shaped and have several external surfaces owning different three-dimensional orientation. They produce more scratches and abrasion. Additionally the occurrence of larger fragments can scarcely be avoided in ground Perlite. Such fragments also lead to more scratches.

The desirable Perlite particles are dome-shaped and have a cornered periphery. Thus, they are not planar but bent in a convex or concave manner. The angles at the edges are about 90°, and the particles are about polygonal. Due to their bent surface, however, the particles form an angle with an underlying material that is much higher than 0°. For the same reason, the cutting edges do not touch the underlying material over their entire lengths but rather punctually. Although Perlite is by far superior to other abrasives, it still works according to the "scratching principle".

The spandrel fragments cannot show any orientation effect, i.e. they can not fall flat under load. Their edges are therefore forming angles of up to 90° with an underlying surface. Thus they produce scratches and induce a generally rough surface.

A further disadvantage of Perlite in the field of dental medicine is the fact that Perlite is a natural material and consequently may display variations in morphology and chemical composition that may have negative effects on the processing. It is therefore necessary to install a costly quality control.

The applicant has found that, besides the aspects discussed above, another material property that has an essential influence on the smooth cleaning of delicate surfaces has not been sufficiently taken into account to date: Known cleaning agents own the property that their abrasive effect but simultaneously also the formation of scratches is increasing along with an increase of the pressure (load) of the application tool. This introduces a great element of uncertainty of use, since cleaning agents are often applied manually. The design of a cleaning agent with an optimal compromise between cleaning effect, abrasive action and scratch formation seems thus nearly impossible.

An objective of the present invention is to describe an abrasive component for cleaning agents intended for use on delicate surfaces where the abrasive effect is less dependent on the pressure (load) that is exerted during its application.

Such an abrasive material is defined in claim 1. Further claims refer to special and preferred embodiments, to formulations using the abrasive component and to applications thereof.

DETAILED DESCRIPTION

Figure 1:
FIG. 1 is a micrograph of glass flakes used as an abrasive component according to an embodiment of the present invention.

Thus, the abrasive component of the invention distinguishes itself by being essentially composed of approximately plate-shaped particles whose sizes vary as little as possible and/or which have a periphery showing only few sharp points: Their shape thus approximates that of a polygon whose corners do not exhibit angles greater than 33° nor smaller than 30°. It is necessary that the edges are absolutely straight, they are, however, preferably straight.

The abrasive material according to the invention may be included in the cleaning agent in a cleaning product. In the context of the description, as a cleaning agent, it is understood the totality of components, which show a cleaning action, of a cleaning product, i. e. beside abrasive materials also surfactants etc. As an abrasive component of a cleaning agent, the totality of materials is understood which show abrasive action and are included in the abrasive component.

Having recognized the advantage of the plate shape, the application has found appropriate synthetic materials. Glass flakes proved best suited. They are a synthetically manufactured material whose properties are essentially adjustable and controllable.

The reduced pressure-dependence of the action of the plate-shaped abrasive component could be explained by the fact that the planar plates will increasingly orient themselves parallel to the surface that is worked on when the pressure (load) of application is increased, thus reducing the abrasive effect. It is further believed that the plates which are sliding in a sharp angle over the surface to be cleaned, will remove adherent deposits from the surface by a planing action, i.e. by sliding between the surface and the deposits and removing the latter with care and along a broad surface. It can further be assumed that the plates will rapidly "sit down" on one edge and that they will touch the surface only very rarely and for a short time by only one corner.

An explanation for the gentle cleaning effect in spite of the relatively large size of the plates may therefore be that they do not much scratch the surface but rather remove adherent deposits by planing or scraping them off. It has also been observed that the mechanical properties of this abrasive component react less sensitively to an occasional presence of larger plates since these also act according to the same mechanism as small ones.

It has further been observed that the cleaning effect of this abrasive component increases with decreasing particle size and thus increasing number of particles. It is believed that this is due to the fact that more edges are available but also that smaller particles will probably rest on one corner for a little longer, giving the "scratching principle" a little more time before the plates fall parallel to the underlying surface and start working according to the "planing principle" of action.

Mica consists of plate-like particles that are, however, mostly too thin and thus too flexible. Furthermore, the edges are often curved and split up into lamellae. The former prevents a linear contact of the edges with the surface to be cleaned, the latter weakens the edges and renders them flexible. These facts are believed to be responsible for the fact that the cleaning effect of mica is sensibly lower than that of glass flakes.

The invention will now be explained in more detail by the description of examples of application thereof and making reference to FIG. 1, which is a micrograph of glass flakes.

As a result of numerous experiments, the Applicant has found the following commercially available product that fits in with the requirements of the invention: Glass flakes RCF-160 (Mühlmeier GmbH, Bärnau, Germany) (see FIG. 1: Plates of borosilicate glass, size about 45 to 300 μm (distribution, see Table 1), thickness about 4 μm.

TABLE 1

| Particle size distribution of RCF-160 | |
|---|---|
| Particle size μm | Proportion (particle frequency) |
| <=68 | 10% |
| <=188 | 50% |
| <=315 | 90% |
| <=1,700 | 100% |

Cleaning experiments, conducted with toothpastes containing the above glass flakes, have resulted in surprisingly little scratching of the treated tooth surfaces. The cleaning effect was, however, similar to that of dentifrice formulations that had been manufactured using known abrasive components. Furthermore, there was a significantly reduced dependence of the cleaning effect and the extent of scratching on the pressure (load) applied during use. It must also be noted that the average particles size of the glass flakes is clearly larger than the respective size of particles in known abrasives, e.g. on Perlite basis. Until now, it has generally been accepted that larger particles will yield a higher cleaning effect but also much more scratches. The mechanical properties of the glass flakes now show that, unlike earlier beliefs, it is possible to combine a good cleaning effect with little scratching or stria formation, along with a reduced dependence on the particle size.

Based on the special aptitude of glass flakes, the following requirements for the particles of an abrasive component according to the invention can be established:

flatness;

defined hardness;

defined thickness to size ratio: The edges are thus sufficiently supported so that there is at the beginning a predominant cleaning action replaced after a short time, e.g. 10 to 15 seconds, by a polishing action that will become increasingly effective due to the wear (rounding off) of the edges of the fragments;

polygonal circumference;
polygon corners having an angle of at least 30°;
straight-line edges;
small proportion, preferably total absence of particles having other shapes;
edge angle about 90°.

It may, however, not be necessary that an abrasive component ideally fulfills all these conditions; it is expected that the effect described by the invention is also brought about by components showing only a partial congruity with the above defined properties depending on the material and the application.

Glass flakes have been used to formulate examples of toothpastes and prophylaxis pastes:

EXAMPLE 1

Toothpaste

| Component | Proportion (weight %) |
| --- | --- |
| Aqueous liquid containing water and glycerol, sorbitol, disaccharide syrup, etc. | 35 to 95% |
| Sweetening agent | 0.1 to 0.5% |
| Organic thickening agent | 0 to 3% |
| Polyethylene glycol | 0 to 6% |
| Preserving agent, fluoride compounds, coloring agents and flavoring agents, pigments | 0.5 to 12% |
| Tenside mixture of sodium laurylsulfate, sodium laurylsarcosinate and a sodium tauride | 2 to 5% |
| Glass flakes RCF-160 | 0.01 to 60% |
| Pyrogenic silicic acid, hydrophilic | 1 to 3% |

EXAMPLE 2

Prophylaxis Paste

| Component | Proportion (weight %) |
| --- | --- |
| Flavoring agent | 2 |
| Cetyl alcohol | 3 |
| Emulsifier (Emulgin R040, Henkel, Germany) | 3 |
| Coloring agent (red iron oxide) | 1.7 |
| Sodium fluoride | 2.8 |
| Glass flakes (RCF-160) | 40 |
| Polyethylene glycol (Macrogol 400) | 43 |
| Sweetening agent (Aspartame ®) | 1 |
| Titanium dioxide | 2 |
| Gel forming agent (Tego Carbomer 141, Goldschmidt AG, Germany) | 1.5 |
| Total | 100 |

Components that are not specified in detail are already known per se for such applications, and a selection may be made from commercially available products according to individual requirements, e.g. for preserving agents, flavoring agents, etc.

Based on the above description, a specialist in the art will be able to modify the compositions without, however, leaving the scope of protection conferred by the invention that is defined by the claims. The following may be considered, for example:

Use of other abrasive materials, preferably synthetically manufactured ones, whose particles
   are essentially plate-shaped;
   are planar, nearly planar or slightly bent; and/or
   have predominantly straight-line edges;
   Production of formulations that have a consistency ranging from semi-solid over pasty to liquid (e.g., mouthwashes, chewing-gums, etc.) incorporating an abrasive component that consists at least in part of an abrasive material described in this invention;
   Formulation and subsequent use of abrasive compositions described in this invention for purposes other than dental hygiene, i.e. in general for the cleaning and care of delicate surfaces;
   Use of other abrasive materials essentially containing abrasive plates which are substantially equivalent to glass flakes, in at least one of the material properties that are determinant for the cleaning effect (shape of the edge; structure of the edges; hardness; etc);
   Use of plate-shaped silicates and naturally occurring glasses, e.g. of volcanic origin;
   Addition of other abrasive materials as further components of the cleaning agent, in particular the use of the known materials listed above.

The invention claimed is:

1. A dental care formulation comprising an abrasive, the abrasive comprising borosilicate glass platelets each having a planar body having a size of about 45–300 μm and a thickness of about 4 μm, wherein the dental care formulation is selected from the group consisting of a toothpaste, prophylaxis paste, chewing gum and mouthwash, and wherein the platelets are able to orient themselves parallel to an oral surface as pressure is applied, thereby reducing their abrasive effect.

2. The dental care formulation according to claim 1 wherein the borosilicate glass platelets comprise corner angles defined by adjoining edges, and wherein the corner angles of the numerical majority of said glass platelets are exclusively between 30° and 330°.

3. The dental care formulation according to claim 2 wherein the edges of said glass platelets are essentially straight in order to secure a linear contact of said glass platelets with an underlying surface to be cleaned in any position of the glass platelets.

4. The dental care formulation according to claim 1 wherein said glass platelets are essentially solid plates, seen in cross section, having angles of about 90° at the transitions to the upper and the lower surfaces of the plates.

5. The dental care formulation according to claim 1 wherein said abrasive consists essentially of said glass platelets.

6. A method for the professional cleaning of teeth comprising applying a dental care formulation according to claim 1 in the form of a prophylaxis paste to a rotatable carrier, contacting a tooth surface with the rotatable carrier having the prophylaxis paste thereon, and rotating the rotatable carrier against the tooth surface to remove adherent deposits from the tooth surface by a sliding motion between the glass platelets and the tooth surface.

7. A method for cleaning of teeth comprising applying a dental care formulation according to claim 1 in the form of a toothpaste to a toothbrush, contacting a tooth surface with the toothbrush having the toothpaste thereon, and moving the toothbrush relative to the tooth surface to clean the tooth surface by a sliding motion between the glass platelets and the tooth surface.

* * * * *